US010058418B2

(12) United States Patent
Righini

(10) Patent No.: US 10,058,418 B2
(45) Date of Patent: Aug. 28, 2018

(54) IMPLANT, INTENDED TO BE PLACED IN A BLOOD CIRCULATION PASSAGE, COMPRISING A SYSTEM FOR SEPARATING THE PROXIMAL ARMS

(71) Applicant: LABORATOIRES INVALV, Dury (FR)

(72) Inventor: Giovanni Righini, Gland (CH)

(73) Assignee: LABORATOIRES INVALV, Dury (FR)

( * ) Notice: Subject to any disclaimer, the term of this patent is extended or adjusted under 35 U.S.C. 154(b) by 389 days.

(21) Appl. No.: 14/785,208

(22) PCT Filed: Apr. 17, 2014

(86) PCT No.: PCT/EP2014/057972
§ 371 (c)(1),
(2) Date: Oct. 16, 2015

(87) PCT Pub. No.: WO2014/170463
PCT Pub. Date: Oct. 23, 2014

(65) Prior Publication Data
US 2016/0095700 A1 Apr. 7, 2016

(30) Foreign Application Priority Data

Apr. 19, 2013 (FR) ...................................... 13 53605

(51) Int. Cl.
A61F 2/24 (2006.01)
(52) U.S. Cl.
CPC .......... A61F 2/2409 (2013.01); A61F 2/2418 (2013.01); A61F 2/2427 (2013.01); A61F 2/2436 (2013.01)
(58) Field of Classification Search
CPC .... A61F 2/2409; A61F 2/2418; A61F 2/2427; A61F 2/2436
See application file for complete search history.

(56) References Cited

U.S. PATENT DOCUMENTS

2011/0313515 A1 12/2011 Quadri

FOREIGN PATENT DOCUMENTS

WO 2009053497 A1 4/2009
WO WO 2011163275 A2 * 12/2011 ........... A61F 2/2415
WO 2013072496 A1 5/2013

OTHER PUBLICATIONS

International Search Report for PCT/EP2014/057972 dated Jun. 20, 2014.

* cited by examiner

Primary Examiner — Ashley Fishback
(74) Attorney, Agent, or Firm — Pearne & Gordon LLP

(57) ABSTRACT

The implant comprises a tubular proximal sleeve, extending between a proximal end and a distal end, and deployable between a contracted configuration and a deployed configuration. Proximal arms each extend between an end connected to the distal end, and a free end positioned past the distal end. At least one proximal arm is elastically deformable between a separating position and an anchoring position, the radial distance between its free end and its connected end being larger in the separating position rather than in the anchoring position. This proximal arm is elastically recalled toward its anchoring position. The implant includes: a first stop, supported by this proximal arm, and a second stop, cooperating with the first stop in the contracted configuration to keep this proximal arm in its separating position, and releasing this first stop in the deployed configuration.

13 Claims, 10 Drawing Sheets

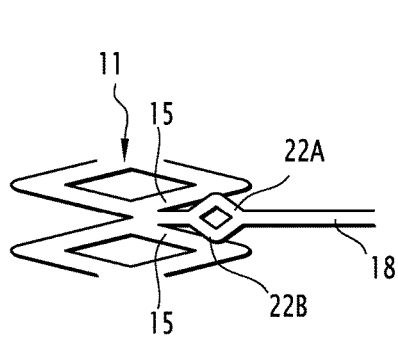
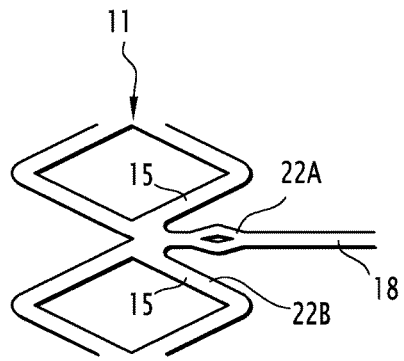
FIG.9    FIG.10
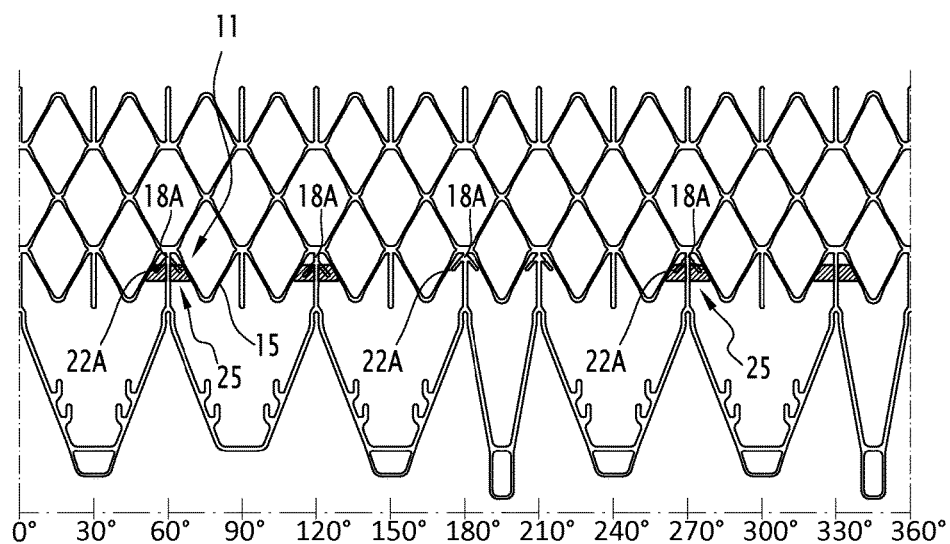
FIG.11

IMPLANT, INTENDED TO BE PLACED IN A BLOOD CIRCULATION PASSAGE, COMPRISING A SYSTEM FOR SEPARATING THE PROXIMAL ARMS

This is a National Stage application of PCT international application CT/EP2014/057972, filed on Apr. 17, 2014 which claims the priority of French Patent Application No. 353605 entitled "IMPLANT, INTENDED TO BE PLACED IN A BLOOD CIRCULATION PASSAGE, COMPRISING A SYSTEM FOR SEPARATING THE PROXIMAL ARMS", filed with the French Patent Office on Apr. 19, 2013, both of which are incorporated herein by reference in their entirety.

The present invention relates to an improved implant designed to be placed in a blood circulation passage, in particular in a cardiac atrioventricular valve.

Such an implant is in particular designed to replace a native heart valve, in particular a mitral valve or a tricuspid valve.

In the case of a mitral valve, the implant is designed to be placed in a blood passage of an atrioventricular valve of a human or animal heart.

During systole, the blood passage between the left atrium and the left ventricle of the heart is interrupted by the closing of a native heart valve present in a mitral apparatus. This valve ensures a unique circulation of the blood flow, avoiding reflux at the end of the ventricular contraction.

The mitral apparatus comprises a mitral annulus, two valvular leaflets connected to that annulus, and a subvalvular apparatus comprising chords and pillars. The valvular leaflets include an anterior leaflet, also called "large mitral valve", and a posterior leaflet, also called "small mitral valve".

The connecting part connecting the annulus to the large mitral valve is fibrous, while the connecting part connecting the annulus to the small mitral valve is muscular. The small and large mitral valves are connected to the ventricular part by chords, which in turn are connected to the pillars. In diastole, the two leaflets open to free the passage between the left atrium and the left ventricle.

In systole, the ventricular contraction creates an abrupt elevation of the left intraventricular pressure, causing blood to be ejected through the aortic valve. At the same time, the contraction of the pillars and the tensing of the chords cause the junction of the leaflets with respect to one another, so as to tightly isolate the left atrial and ventricular cavities.

However, diseases affect the valves and the chords. In particular, these may suffer from degeneration, thus allowing reflux or regurgitation.

Furthermore, in case of severe and chronic mitral regurgitation, the underlying left ventricle expands and its ability to contract decreases, which can lead to the need for a heart surgery, even when there are no symptoms.

In order to resolve these problems, it is known to place an implant between the leaflets defining the sick valve. The implant for example includes a deployable tubular endoprosthesis and a flexible closing member made from animal tissue. The flexible closing member is permanently fastened in the endoprosthesis.

Such implants can generally be implanted less invasively than a surgical valve replacement, which limits the risks associated with the implantation of the valve, in particular in terms of mortality.

For example, known from WO 2010/121076 is a mitral implant positioned in an atrioventricular blood passage to replace the native valve.

Such an implant includes a plurality of atrial arms (also called "distal arms"), and a plurality of ventricular arms (also called "proximal arms") positioned across from the atrial arms to pinch the mitral annulus, while bearing on the atrial face of the leaflets of the native valve while plicating it. The ventricular arms are formed by hooks positioned at the ventricular end of the armature and folded toward the atrial end. The atrial arms are formed by V-shaped loops extending across from the ventricular arms, near the latter, but moving away from the armature and the atrial arms.

The ends of the ventricular arms and the atrial arms are positioned away from one another and are respectively pushed into an atrial face and a ventricular face of the mitral annulus.

Another implant example is in particular described in WO 2011/057087.

It will be noted that the installation of a mitral implant to replace the native valve can be done by passing through the atrial cavity, or alternatively by passing through the ventricular cavity. This installation is generally done using an appropriate release tool. The structure of this release tool can be different depending on the side (atrial or ventricular) passed through to perform this installation.

The invention in particular aims to facilitate the installation of a mitral implant, in particular when the latter is installed by passing through the ventricular cavity.

To that end, the invention in particular relates to an implant designed to be placed in a blood circulation passage, and to be fastened on a tissue, and comprising:

a proximal sleeve, generally tubular around a central axis, extending longitudinally between a proximal end and a distal end, the proximal sleeve being deployable between a contracted configuration and a deployed configuration, a plurality of proximal arms, each extending between a first end connected to the distal end of the proximal sleeve, and a second free end designed to bear on a first face of the tissue, each proximal arm extending in the direction of the central axis such that its free end is positioned beyond the distal end of the proximal sleeve, a distal sleeve, with a generally tubular shape around the central axis, deployable between a contracted configuration and a deployed configuration, designed to be assembled with the proximal sleeve to form a tubular armature together, that armature defining an internal blood circulation conduit when the proximal sleeve and the distal sleeve are assembled and each in the deployed configuration, a plurality of distal arms, supported by the distal sleeve, and extending substantially perpendicular to the central axis in the deployed configuration, designed to bear on a second face of the tissue, such that the tissue is then pinched between the proximal arms and the distal arms, characterized in that:

at least one proximal arm is elastically deformable, between a separating position and an anchoring position, such that, when there is no outside bias, the radial distance between its free end and its connected end is larger in the separated position rather than in the anchoring position, this proximal arm being elastically returned toward its anchoring position, the implant includes means for maintaining said at least one deformable proximal arm in its separating position, comprising:

a first stop, supported by that proximal arm, and a second stop, designed to cooperate with the first stop when the proximal sleeve is in the contracted configuration to keep that proximal arm in its separating position, and to release that first stop when the proximal sleeve is in the deployed configuration to allow the proximal arm to move toward its anchoring position.

Each proximal arm extends from the distal end of the proximal sleeve past that distal end. Thus, when the proximal sleeve is brought closer to the valve leaflets from the ventricular cavity, the proximal arms are located in front of that proximal sleeve, such that they can receive the valve leaflets without being bothered by that proximal sleeve.

Thus, the structure of the implant defined above allows very easy insertion of the valve leaflets in a receiving space defined by the proximal arms.

Furthermore, owing to the maintaining means, the separation of the proximal arms is ensured and optimized during the installation of the implant.

It should be noted that the proximal sleeve and the distal sleeve together form an implant body when they are assembled. Thus, the implant body is considered to be formed only when these proximal and distal sleeves are assembled.

An implant according to the invention can further include one or more of the following features, considered alone or according to any technically possible combinations.

The first stop of the proximal arm extends laterally relative to that proximal arm, the first stop preferably being arranged near the connected end of that proximal arm.

The second stop is supported by the proximal sleeve.

The proximal sleeve is formed by different filiform elements arranged in a grid, forming cells, for example diamond-shaped cells, each proximal arm provided with a first stop being arranged circumferentially on the proximal sleeve between two consecutive cells, the corresponding second stop being supported by at least one of the filiform elements forming those two consecutive cells, those filiform elements being brought closer to one another in the contracted configuration, such that the second stop cooperates with the first stop, and separated from one another in the deployed configuration, so as to leave a radial passage for the first stop, thus releasing that first stop.

The proximal sleeve supports at least two proximal arms each provided with a first stop, such that the distance between the first stop and the connected end of one of those two proximal arms is greater than the distance between the first stop and the connected end of the other of those two proximal arms.

The first stop of at least one of the proximal arms is formed by a protruding part of that proximal arm, extending laterally relative to that proximal arm.

The first stop of at least one of the proximal arms is formed by an element attached on that proximal arm, for example welded, that element extending laterally relative to that proximal arm.

The invention also relates to a treatment device for a blood circulation passage, in particular in a heart atrioventricular valve, characterized in that it includes an implant as previously defined, and a release tool for that implant, the proximal and distal sleeves being mounted in their contracted configurations in that release tool.

A treatment device according to the invention can further comprise one or more of the following features, considered alone or in combination:

The release tool includes a maintaining sheath of each proximal arm provided with a first stop in its separating position, said maintaining she has a general shape of revolution around the longitudinal axis, and is designed to be positioned around the proximal sleeve in the contracted configuration, said maintaining sheath includes longitudinal strips separated by longitudinal openings, each longitudinal strip being designed to route through an opening provided in a respective proximal arm, and each longitudinal strip includes a second stop designed to cooperate with the first stop of the proximal arm through which the longitudinal strip passes.

Said longitudinal strip is provided with a boss, protruding radially toward the outside of the maintaining sheath, bearing said second stop.

The invention also relates to a method for installing an implant as previously defined, on the leaflets of a native valve, between an atrial cavity and a ventricular cavity of the heart, the leaflets having an atrial face and a ventricular face, the method including:

a step for positioning the distal arms in the atrial cavity,
a step for deploying said distal arms in the atrial cavity,
a step for pressing the distal arms against the atrial face of the leaflets,
a step for moving the proximal sleeve toward the leaflets, with the proximal arms deployed so as to define a receiving space for the leaflets, in order to insert the leaflets into the receiving space, and pressing the proximal arms against the ventricular face of the leaflets by applying an axial force toward those leaflets,
a step for deploying the distal sleeve and the proximal sleeve, and assembling the distal sleeve with the proximal sleeve so as to form a tubular armature of the implant.

Advantageously, the method uses a release tool in which the implant is housed in the contracted position, the tool including:

an inner sheath for keeping the distal sleeve in the contracted configuration, and keeping the distal arms in the axial configuration,
an outer sheath for keeping the proximal sleeve in the contracted configuration.

In this case, the method includes:

a step for deploying the proximal arms, in particular by retracting the outer sheath so as to release the proximal arms,
a step for positioning the distal arms in the atrial cavity, while the inner sheath is still positioned around the distal arms,
a step for deploying the distal arms in the atrial cavity, while retracting the inner sheath so as to free those distal arms,
a step for pressing the distal arms against the atrial face of the leaflets, by moving the tool toward the ventricular cavity so as to apply an axial force toward that ventricular cavity,
a step for moving the proximal sleeve toward the leaflets, while the outer sheath covers the proximal sleeve, and pressing the proximal arms against the ventricular face of the leaflets to apply an axial force oriented toward the atrial cavity,
a step for applying the proximal and distal sleeves, while retracting the inner and outer sheaths.

According to one advantageous embodiment:

the step for positioning the distal arms in the atrial cavity takes place after the step for deploying the proximal arms, the step for deploying the distal arms in the atrial cavity takes place after the step for positioning the distal arms in the atrial cavity, the step for pressing the distal arms against the atrial face of the leaflets follows the step for deploying the distal arms in the atrial cavity, the step for moving the proximal sleeve toward the leaflets is done following the pressing of the distal arms against the atrial face of the leaflets, the step for deploying the proximal and distal sleeves takes place after moving the proximal sleeve toward the leaflets.

According to another embodiment:

the outer sheath and the proximal sleeve in the contracted configuration in the outer sheath are introduced into the ventricular cavity by a first route, and the inner sheath and the distal sleeve in the contracted configuration in the inner sheath are introduced into the atrial cavity by a second route different from the first.

The native valve is chosen between a mitral valve or a tricuspid valve.

The invention will be better understood using the following description, provided solely as an example and done in reference to the appended figures, in which:

FIGS. 9 and 10 are views similar to FIGS. 7 and 8 of maintaining means according to a third example embodiment, when the proximal sleeve is in the contracted and deployed configurations, respectively;

FIG. 11 shows a proximal sleeve, shown unwound, comprising maintaining means according to a fourth example embodiment of the invention;

FIGS. 14 to 20 diagrammatically show, in axial cross-section, a treatment device according to the invention, shown in different release phases of the implant;

FIGS. 21 to 26 diagrammatically show, in axial cross-section, a treatment device according to the invention, shown in different release phases of the implant according to a second embodiment of the release;

FIGS. 27 to 32 diagrammatically show, in axial cross-section, a treatment device according to the invention, shown in different release phases of the implant according to a third embodiment of the release.

Figure 1:
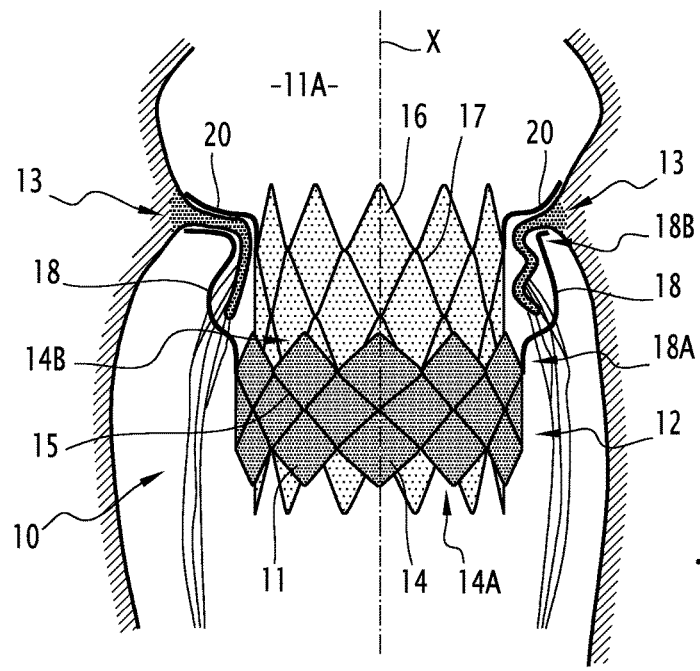
FIG. 1 is a diagrammatic profile view of an implant according to one example embodiment of the invention, positioned in a blood circulation passage, in a cardiac atrioventricular valve.

FIG. 1 shows an implant 10 designed to be positioned and deployed in a blood circulation passage, for example in a passage situated in a patient's heart.

The implant 10 is advantageously a heart valve designed to replace a defective native valve, more particularly an atrioventricular valve. Thus, the implant 10 is advantageously designed to replace the native mitral valve situated between a left atrium 11A and a left ventricle 11B of the heart, so as to allow a unique circulation of the blood flow between that left atrium 11A and that left ventricle 11B.

Alternatively, the implant is an atrioventricular valve, designed to replace the heart valve in the tricuspid position. It should be noted that, in this case, the implant can be added via a transventricular route, or alternatively via a transjugular route.

The implant 10 is in particular designed to be fastened on a tissue 13 of the heart, that tissue 13 in the illustrated example being formed by native valve leaflets.

The implant 10 includes a tubular armature 12, designed to define an inner blood flow conduit. This armature 12 is advantageously provided with a closing member (not shown) that is tissue-based, in particular synthetic or natural tissue, such as bovine, equine and/or porcine pericardium. This closing member is designed to ensure the unique circulation of the blood through this armature 12.

The tubular armature 12 includes a proximal sleeve 14 and a distal sleeve 16, attached on one another and assembled to form the armature 12.

It should be noted that the tubular armature 12 cannot be considered to be formed until the proximal sleeve 14 and the distal sleeve 16 are assembled.

The proximal sleeve 14 has a generally tubular shape around a central axis X. This proximal sleeve 14 extends longitudinally, toward the central axis X, between a proximal end 14A and a distal end 14B. This proximal sleeve 14 can be deployed between a contracted configuration (which will be described later, in particular in reference to FIGS. 2 and 3) and a deployed configuration (which will be described later, in particular in reference to FIG. 4).

The implant 10 further includes a plurality of proximal arms 18, each extending between a first end 18A connected to the distal end 14B of the proximal sleeve 14, and a second free end 18B designed to press on a proximal face of a valve leaflet 13. The proximal sleeve 14 therefore forms, with the proximal arms 18, a first single-piece assembly.

Each proximal arm 18 extends in the direction of the central axis X, such that its free end 18B is positioned beyond the distal end 14B of the proximal sleeve 14.

The proximal arms 18 being designed to press on the valve leaflets 13 on the left ventricle side, these proximal arms 18 are also called "ventricular arms".

In the example of FIG. 1, the proximal arms 18 have a wavy profile shape, such that each proximal arm 18 includes, between its connected end 18A and its free end 18B, at least one intermediate region extending along and radially away from the armature 12 to define a longitudinal housing for receiving a valve leaflet.

According to one preferred alternative, each proximal arm 18 includes two branches distally converging toward one another to have substantially an upside down V shape in the deployed configuration. Such proximal arms 18 are in particular shown in FIG. 11.

Advantageously, two adjacent proximal arms 18 have a shared part from which a respective branch of each of those proximal arms extends. Thus, each proximal branch 18 includes two connecting parts with the proximal sleeve, each of those connecting parts being shared by a respective adjacent proximal arm, as shown in FIG. 11 in particular.

The connecting parts of a proximal arm 18 form its connected end 18A.

Advantageously, the shapes of the proximal arms 18 are adapted to the predetermined configuration of the blood circulation passage designed to receive the implant 10. Thus, for example, at least one proximal arm 18 has a length greater than that of at least one other proximal arm. Alternatively or in combination with said greater length, the transverse distance between the connecting parts of at least one proximal arm is smaller than that between the connecting parts of at least one other proximal arm.

The distal sleeve 16 also has a general tubular shape around the central axis X. This distal sleeve 16 is also deployable between a contracted configuration and a deployed configuration. More particularly, the distal sleeve 16 is designed to be assembled with the proximal sleeve 14 to form the tubular armature 12 of the implant 10 when this proximal sleeve 14 and this distal sleeve 16 are assembled, each in a deployed configuration.

The implant 10 also includes a plurality of distal arms 20, each being supported by the distal sleeve 16, and extending substantially perpendicular to the central axis X when this distal sleeve 16 is in its deployed configuration. Thus, the distal sleeve 16 forms, with the distal arms 20, a second single-piece assembly, designed to be attached on the first assembly.

The distal arms 20 are designed to bear on a distal face of a valve leaflet 13, i.e., on the side of the left atrium, also called atrial cavity, when the valve is a mitral valve. Thus, these distal arms 20 are also called "atrial arms".

Each distal arm 20 for example forms a loop protruding transversely relative to the central axis X.

When the implant 10 is installed in the blood circulation conduit, the valve leaflets 13 are pinched between the proximal arms 18 and the distal arms 20, thus ensuring anchoring of the implant 10, as shown in FIG. 1.

It will be noted that the implant 10 is said to be "in the deployed configuration" when the proximal sleeve 14 and the distal sleeve 16 are assembled in the deployed configuration. Conversely, the implant 10 is said to be "in the contracted configuration" when it is positioned in a release tool 19, in which the proximal 14 and distal 16 sleeves are positioned in contracted configurations, as will be described later, in particular in reference to FIGS. 14 to 20.

Advantageously, each of the proximal 14 and distal 16 sleeves, therefore also the implant 10, is self-expanding, i.e., its deployed configuration is its idle position. Thus, each of the proximal 14 and distal 16 sleeves, therefore also the implant 10, in its contracted configuration, is elastically biased toward its deployed configuration.

For example, the proximal sleeve 14, the distal sleeve 16, the proximal arms 18 and the distal arms 20 are formed from a stainless steel having elastic properties. Alternatively, these elements are made with a base of a shape memory metal such as nitinol (nickel/titanium) or a flexible polymer fiber.

The proximal sleeve 14 is for example formed by a lattice of interlaced filiform elements 15, defining cells M, for example polygonal cells, preferably diamond-shaped cells.

Likewise, the distal sleeve 16 is for example formed by a lattice of interlaced filiform elements 17, defining cells, for example polygonal cells, preferably diamond-shaped cells.

Advantageously, when the proximal sleeve 14 is separated from the distal sleeve 16, and when there is no outside bias, said proximal sleeve has a diameter smaller than that of the distal sleeve 16 without outside bias. Thus, when the distal sleeve 16 is deployed inside the proximal sleeve 14, it exerts a radial force on an inner surface of the proximal sleeve 14, that radial force being sufficient to ensure the connection between the proximal sleeve 14 and the distal sleeve 16.

Furthermore, the distal sleeve 16 has a length, in the direction of the axis X, greater than the length of the proximal sleeve 14. Thus, the proximal sleeve 14 can be positioned in different positions on the distal sleeve 16, in particular based on the configuration of the blood circulation passage designed to receive the implant 10. To that end, the proximal 14 and distal 16 sleeves are movable axially relative to one another before assembly.

Figure 3:
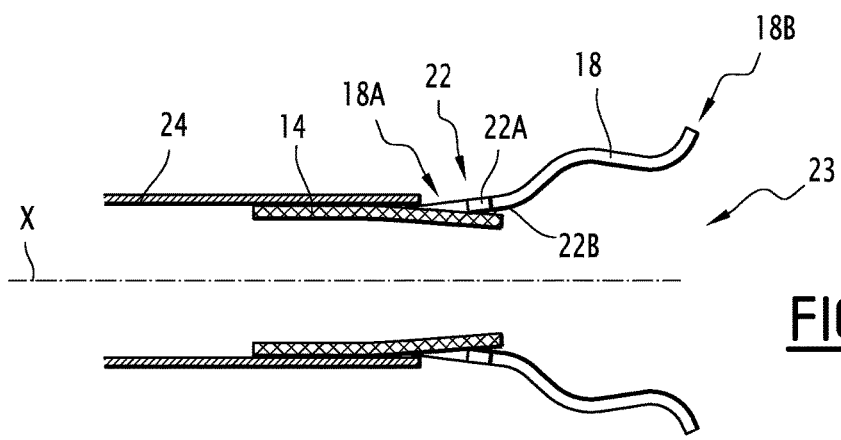
FIG. 3 is a diagrammatic profile view of the sleeve of FIG. 2, in the contracted configuration, whereof the proximal arms are in the separated position.
Figure 4:
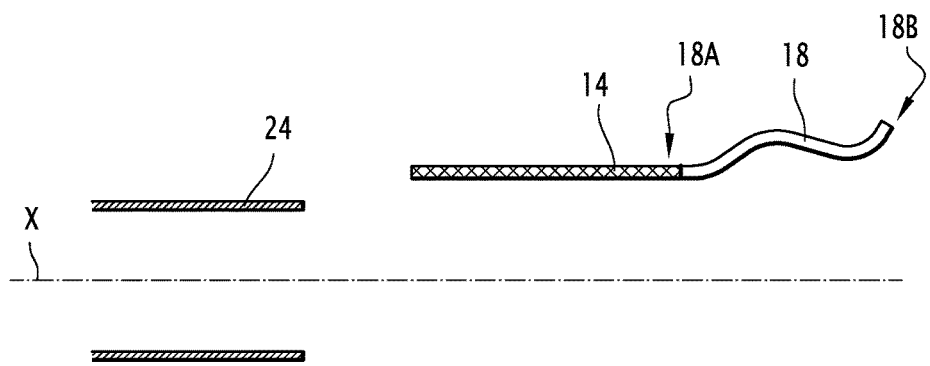
FIG. 4 is a diagrammatic profile view of the proximal sleeve of FIGS. 2 and 3, in the deployed configuration.

According to the invention, at least one of the proximal arms 18, preferably each proximal arm 18, is elastically deformable between a separated position, in particular shown in FIG. 3, and an anchoring position, in particular shown in FIGS. 1 and 4, such that when there is no outside bias, the radial distance between its free end 18B and its connected end 18A is greater in the separating position rather than the anchoring position. It will be recalled that this radial distance is the difference between the distance between the free end 18B and the central axis X, perpendicular to the central axis X, and the distance between the connected end 18A and the central axis X, perpendicular to that central axis.

Each of these proximal arms 18 is elastically recalled toward its anchoring position. Conversely, the implant 10 includes means 22 for maintaining at least one of these deformable proximal arms 18 in its separating position.

The maintaining means 22 comprise at least one first stop 22A supported by this proximal arm 18, and at least one second stop 22B, designed to cooperate with the first stop 22A when the proximal sleeve 14 is in the contracted configuration, to keep the proximal arm in its separating position, and to release the first stop 22A when the proximal sleeve 14 is in the deployed configuration.

Figure 5:
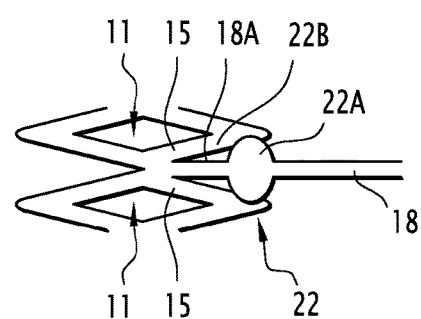
FIG. 5 shows a detail of the proximal sleeve of FIGS. 2 to 4, showing maintaining means, according to a first example embodiment, of a proximal arm in its separating position, these maintaining means being seen from the front.
Figure 6:
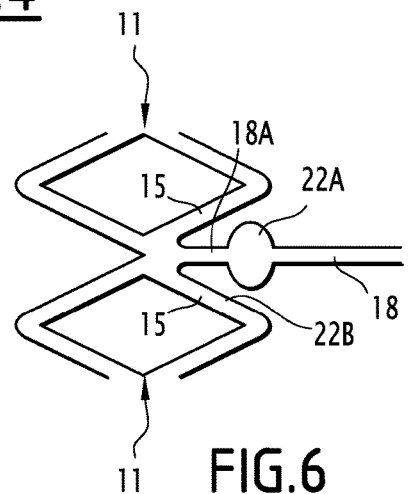
FIG. 6 is a view similar to FIG. 5, showing the maintaining means when the proximal sleeve is in the deployed configuration, and the proximal arms are in the anchoring position.

A first example embodiment of the maintaining means 22 is shown in FIGS. 5 and 6.

According to this first embodiment, the first stop 22A of each proximal arm 18 is supported by a portion of the proximal arm 18, extending laterally relative to the proximal arm 18. "Lateral extension" means that this portion extends in particular in a direction substantially perpendicular to the general longitudinal direction of the proximal arm 18, and substantially parallel to the axis X.

In particular, according to this first embodiment, the first stop 22 is formed by a widening of the proximal arm 18 in this lateral direction. This widening for example is generally oval-shaped.

The first stop 22A is preferably arranged near the connected end 18A of this proximal arm 18.

Furthermore, the second stop 22B is supported by the proximal sleeve 14. More particularly, each proximal arm 18 being arranged circumferentially on the proximal sleeve 14 between two cells M, circumferentially consecutive with the distal end 14B of the proximal sleeve 14, the second stop 22B is supported by at least one of the filiform elements 15 forming these two consecutive cells M.

These filiform elements 15 are brought closer to one another in the contracted configuration, as shown in FIG. 5, such that the second stop 22B cooperates with the first stop 22A.

However, these filiform elements 15 are separated from one another in the deployed configuration, as shown in FIG. 6, so as to leave a radial passage for the first stop 22A, thus freeing that first stop 22A.

Thus, in the contracted configuration of the proximal sleeve 14, the proximal arm 18 is forced into its separating position. However, in the deployed configuration, the proximal arm 18 is elastically returned toward its anchoring position.

Figure 2:
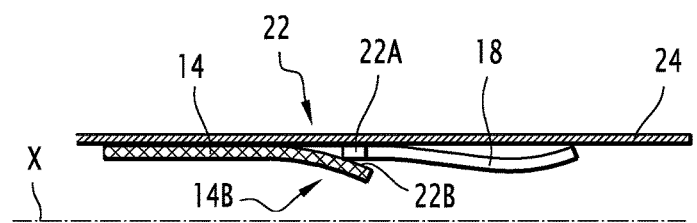
FIG. 2 is a diagrammatic profile view of a proximal sleeve of the implant FIG. 1, when the proximal sleeve is positioned in a sheath of a release tool for the implant.

As an illustration, the proximal sleeve 14 is shown in different stages of its deployment in FIGS. 2 to 4.

In FIG. 2, the proximal sleeve 14 is forced into its contracted configuration by a sheath 24 of the release tool 19 of the implant 10. This sheath 24 therefore applies an outside bias on the proximal arms 18 and on the proximal sleeve 14.

In this sheath 24, the proximal sleeve 14 being in its contracted position, the first stop 22A of each proximal arm 18 is in contact with the corresponding second stop 22B, this first stop 22A being situated radially outside the proximal sleeve 14 relative to the second stop 22B. Thus, each proximal arm 18 is forced toward its separated position by the maintaining means 22. However, due to the outside bias applied by the sheath 24, the proximal arms 18 cannot move away from one another outwardly, such that the second stop 22B is forced toward the inside of the distal sleeve 14 in reaction.

In FIG. 3, the sheath 24 has been slid longitudinally in the direction of the central axis X, so as to free the proximal arms 18 from the proximal sleeve 14. When there is no outside bias applied by the sheath 24, these then deploy in their separating position, under the effect of the constraint exerted by the maintaining means 22.

It is in this configuration that the proximal sleeve 14 is installed in the blood circulation conduit. Indeed, the separation of the proximal arms 14 in particular makes it possible to facilitate the insertion of the valve leaflets 13 in a space 23 for receiving those valve leaflets, defined between the proximal arms 18. It will be noted that the proximal sleeve 14 extends completely (or alternatively, in majority) outside this receiving space 23, such that it does not hinder the insertion of the valve leaflets 13 in this receiving space 23.

Once the proximal sleeve 14 is in place in the blood circulation conduit, the sheath 24 is again slid longitudinally so as to free the proximal sleeve 14. The latter, in the absence of this outside bias, deploys in a deployed configuration. FIG. 4 shows this freed proximal sleeve, in the deployed configuration.

In this deployed configuration, the filiform elements 15 of two component cells M framing each proximal arm 18 are separated from one another, as shown in FIG. 6, leaving a radial passage for the first stop 22A, thus freeing this first stop 22A. Each proximal arm 18 is therefore no longer biased by the maintaining means 22, and it is therefore elastically returned to its anchoring position, in which the free end 18B of this proximal arm 18 bears against one of the valve leaflets 13.

It will be noted that the first stop 22A can assume any suitable considered form.

Figure 7:
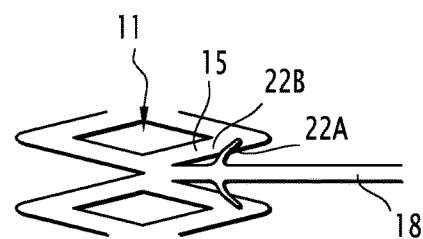
FIGS. 7 and 8 are views similar to FIGS. 5 and 6, showing maintaining means, according to a second example embodiment, when the proximal sleeve is in the contracted and deployed configurations, respectively.
Figure 8:
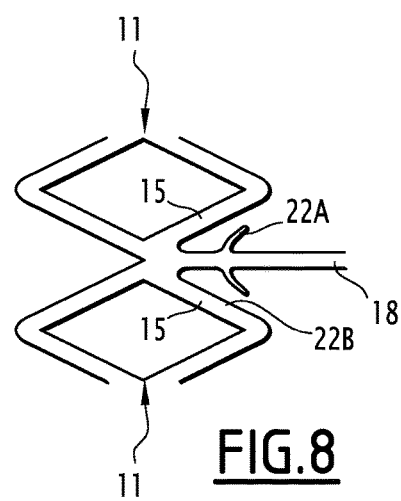

For example, according to a second embodiment shown in FIGS. 7 and 8, the first stop 22A is supported by tabs extending laterally protruding from the proximal arm 18. Each of these tabs is able to bear against a second stop 22B formed by a filiform element 15 of the corresponding cell M framing this proximal arm 18.

According to the third embodiment shown in FIGS. 9 and 10, the first stop 22A is supported by a shape produced by cutting and deformation of the proximal arm 18, this form then extending laterally, protruding from this proximal arm 18.

In this case, each proximal arm 18 is advantageously longitudinally compressed in its separating position, as shown in FIG. 9, such that the cut form extends laterally. However, each proximal arm 18 is advantageously stretched longitudinally in its anchoring position, as shown in FIG. 10, such that the cut form contracts laterally. In this case, suitable means are then provided to compress and longitudinally stretch each proximal arm.

According to a fourth embodiment shown in FIG. 11, the first stop 22A of at least one of the proximal arms 18 is formed by an element 25 attached on the proximal arm 18, for example by welding, this element extending laterally relative to this proximal arm 18.

This element 25 is for example formed by a metal plate welded on the proximal arm 18.

Advantageously, as shown in this FIG. 11, the first stop 22A of a proximal arm 18 can be positioned closer to or further from the connecting end of this proximal arm 18. More particularly, the proximal sleeve 14 bears at least two proximal arms 18 each provided with a first stop 22A, such that the distance between the first stop 22A and the connected end 18A of one of these two proximal arms 18 is greater than the distance between the first stop 22A and the connected end 18A of the other of these two proximal arms 18.

The distance between the first stop 22A and the connected end 18A of a proximal arm 18 is in particular chosen so as to ensure optimal maintenance of this proximal arm 18 in its separated position.

As can also be seen in FIG. 11, in the event two adjacent proximal arms 18 share a common connecting part, each first stop 22A is also advantageously shared by two adjacent proximal arms 18, and to that end arranged on said common connecting part.

Figure 12:
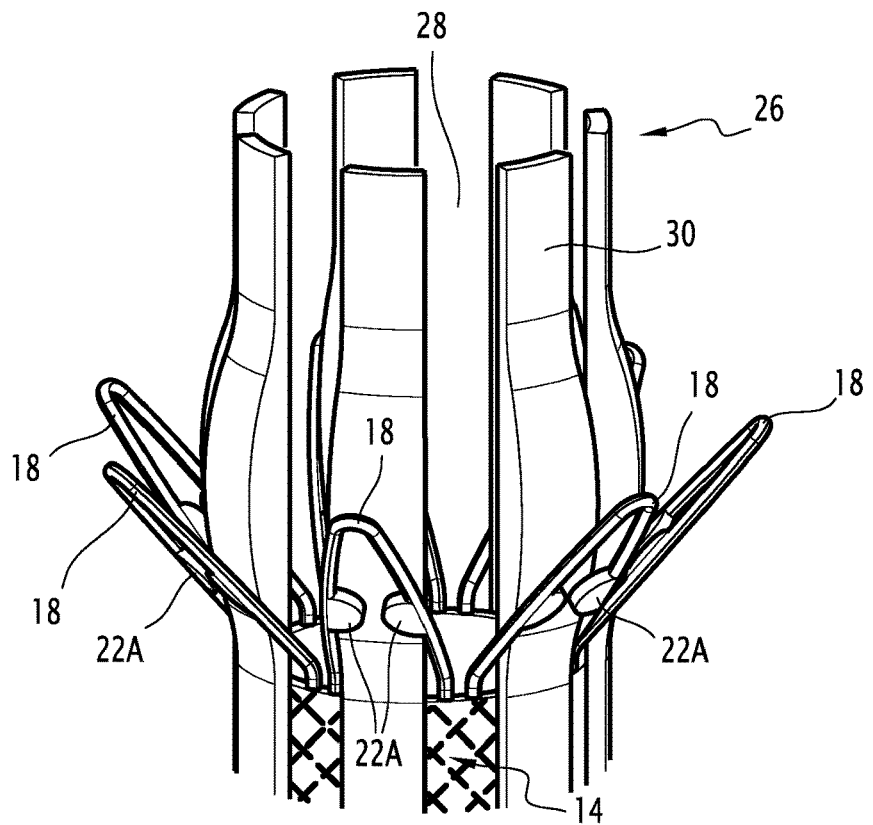
FIG. 12 is a diagrammatic perspective view of a proximal sleeve including maintaining means according to a fifth example embodiment of the invention.
Figure 13:
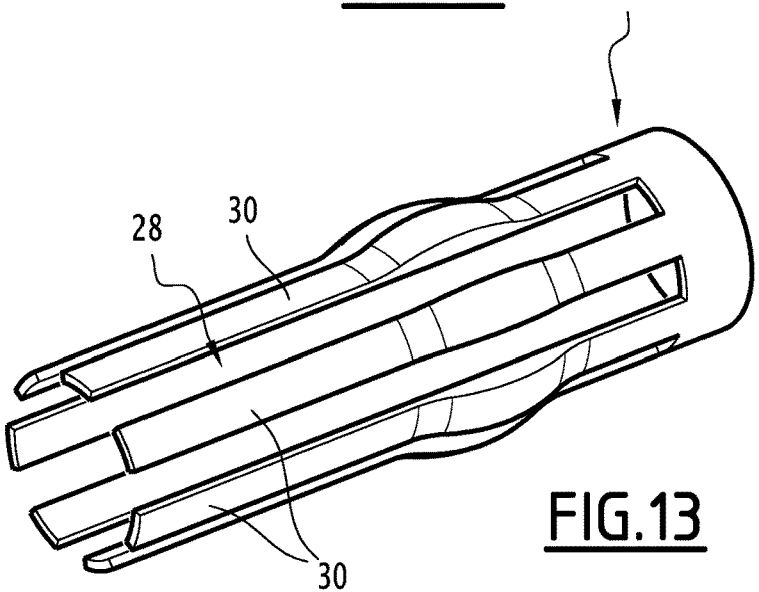
FIG. 13 is a perspective view of a maintaining sheath of the maintaining means of FIG. 12.

According to a fifth embodiment, shown in FIGS. 12 and 13, each second stop 22B is supported by a maintaining sheath 26, shown in FIG. 13.

This maintaining sheath 26 has a general shape of revolution around the longitudinal axis X, and is designed to be positioned around the proximal sleeve 14 in the contracted configuration, as shown in FIG. 12.

This maintaining sheath 26 includes longitudinal strips 30 separated by longitudinal openings 28. Each longitudinal strip 30 is designed to pass through an opening provided in a respective proximal arm 18. Such an opening is for example defined between two branches of the proximal arm 18, when this proximal arm is V-shaped as shown in FIG. 12.

In this case, each proximal arm includes at least one first stop 22A, extending laterally towards said opening, so as to cooperate with at least one respective second stop 22B supported by the longitudinal strip 30 passing in that opening. Each first stop 22A is then supported by an edge of said opening, for example by a branch of the proximal arm 18, and protrudes toward the inside of said opening.

It should be noted that such a maintaining sheath 26 is also compatible with proximal arms having shapes similar to those of the proximal arms shown in FIG. 11.

Each longitudinal strip 30 is advantageously provided with a boss, protruding radially toward the outside of the sheath 26, this boss supporting the second stop 22B. Thus, by sliding the sheath longitudinally, it is possible to vary the radial thickness of this boss, therefore the radial distance between the second stop 22B in contact with the first stop 22A and the central axis X. Thus, it is possible to vary the separation of the proximal arms 18, in order to adapt optimally to the configuration of the blood circulation passage, in particular by deploying the proximal arms 18 in their separating position only when necessary.

It will be noted that the maintaining sheath 26 is for example formed by the sheath 24 of the release tool, described previously in reference to FIGS. 2 to 4, or formed by an additional sheath.

Figure 14:
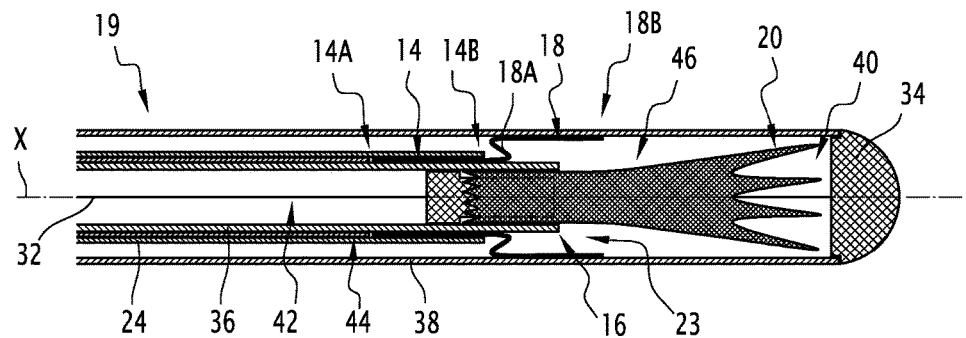

FIG. 14 shows a treatment device, comprising the release tool 19, receiving an implant 10 as previously defined. In this figure, and the following ones, the elements similar to those of the preceding figures are designated by identical references.

As previously indicated, the implant 10 includes a first single-piece assembly including the proximal sleeve 14 of the armature and the proximal arms 18, and a second single-piece assembly including the distal sleeve 16 of the armature and the distal arms 20.

The proximal sleeve 14 extends, along the central axis X, between its proximal end 14A and its distal end 14B. The connected end 18A of each proximal arm 18 is connected to the distal end 14B of the proximal sleeve 14, and the free end 18B of each proximal arm 18 extends in the direction of the central axis X beyond that distal end 14B of the proximal sleeve 14.

The release tool 19 includes an inner rod, provided with a head 34 for maintaining one end of the implant 10, and a stay 32 mounted sliding coaxially on the rod.

The release tool 19 further includes an inner sheath 36, mounted sliding relative to the stay 32, an intermediate sheath 24 mounted sliding around the inner sheath 36, and an outer sheath 38 mounted sliding around the intermediate sheath 24.

It will be noted that the intermediate sheath 24 is the sheath surrounding the proximal sleeve 14, as previously described in reference to FIGS. 2 to 4. Likewise, in the case where the maintaining means 22 include a maintaining sheath 26, as previously described in reference to FIGS. 13 and 14, the intermediate sheath is formed by this maintaining sheath.

It should also be noted that alternatively, the release tool 19 could include, instead of an intermediate sheath and an outer sheath, only an outer sheath performing the functions of said intermediate sheath and said outer sheath.

The stay 32 and the sheath 36, 24, 38 are slidably movable, independently of one another, and relative to the rod.

Locking members (not shown) are generally provided between the rod and the stay 32, between the stay 32 and the sheath 36, 24, 38 to avoid spontaneous sliding of the stay 32 and the outer 38, sheath 24 and inner 36 sheaths. This makes it possible to proceed, through successive steps, with the removals of the outer sheath 38, the intermediate sheath 24, and the inner sheath 36.

The head 34 delimits a housing 40 for receiving the implant 10, in which this implant 10 is kept in the contracted configuration.

More particularly, the stay 32 and the inner sheath 36 define an inner annular space 42 between them, designed to receive the distal sleeve 16 and the distal arms 20. Thus, the distal sleeve 16 is kept in the contracted configuration by the inner sheath 36.

The inner sheath 36 and the intermediate sheath 24 define, between them, an intermediate annular space 44, designed to receive a proximal sleeve 14. Thus, the proximal sleeve 14 is kept in the contracted configuration by this intermediate sheath 24, as previously described.

The outer sheath 38 and the intermediate sheath 24 define an outer annular space 46 between them, designed to receive the proximal arms 18. Thus, each proximal arm 18 is pressed against the outer sheath 38 when it is not covered by the intermediate sheath 24, and the proximal sleeve 14 is in the contracted configuration, as shown in FIG. 3.

When the implant 10 must be positioned, in particular to replace a native valve, it is inserted between the leaflets 13 of the native valve around the seat of the valve. This introduction can be done, using the device of FIG. 14, by passing through the left ventricle, as will be described below in reference to FIGS. 15 to 20.

Figure 15:
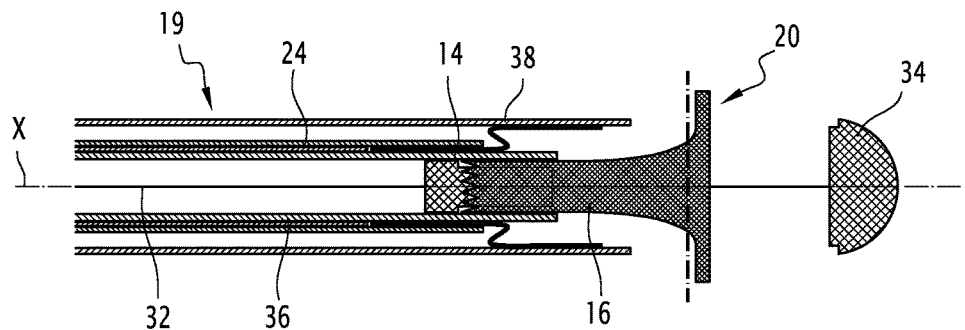

As shown in FIG. 15, the head 34 and the downstream part of the tool 19 are inserted into the atrial cavity, past the mitral annulus, such that the distal arms 20 are positioned in the atrial cavity beyond the mitral annulus.

The outer sheath 38 is retracted axially away from the head 34 relative to the intermediate sheath 24, the inner sheath 36 and relative to the stay 32, to expose the distal arms 20, which then deploy. The tool 19 is then moved toward the left ventricle to press the distal arms 20 against the atrial face of the leaflets 13.

Figure 16:
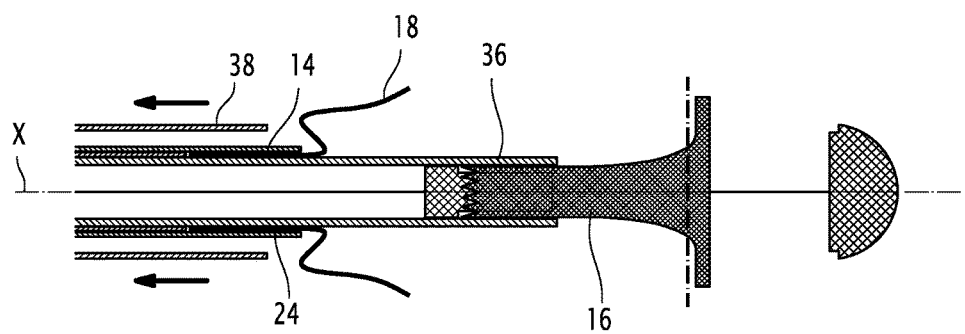

As shown in FIG. 16, the outer sheath 38 is again retracted axially to expose the proximal arms 18. The latter, which were kept pressed against this outer sheath 38, then deploy, under the effect of the constraint imposed by the maintaining means 22. Indeed, the proximal sleeve 14 is kept in its contracted configuration, and the proximal arms 18 are not subject to any outside bias, such that they are then constrained in their separating position by the maintaining means 22, as previously described.

The separation of the proximal arms 18 is then done optimally so that the leaflets 13 are across from a receiving area 23 defined between these proximal arms 18.

Figure 17:
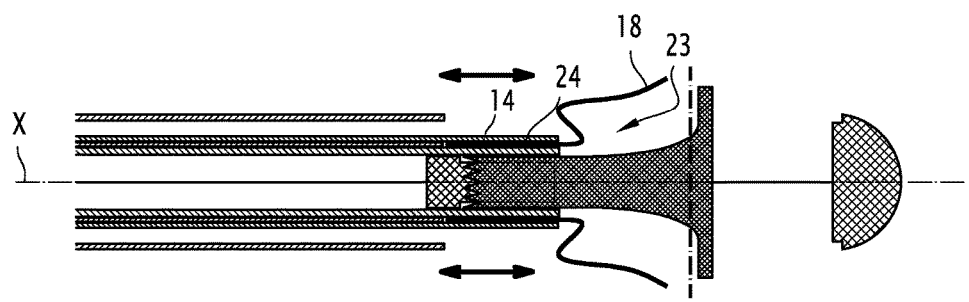

As shown in FIG. 17, it suffices to move the proximal sleeve 14 and the intermediate sheath 24 that surrounds it toward the leaflets 13. These leaflets 13 are thus inserted into the receiving area 23 defined between the proximal arms 18. Because the proximal arms 18 extend past the distal end 14B of the proximal sleeve 14, this proximal sleeve 14 does not hinder the insertion of the leaflets 13 into this receiving area 23.

Figure 18:
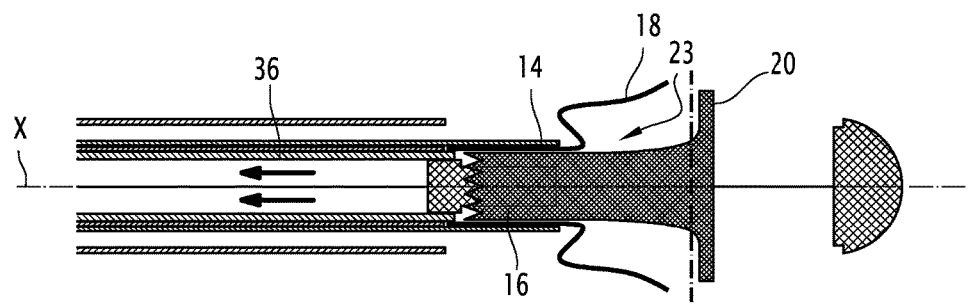

Once the proximal sleeve 14 is in place, the inner sheath 36 is retracted so as to free the distal sleeve 16, as shown in FIG. 18. This distal sleeve 16 being positioned inside the proximal sleeve 14, it is kept in a contracted configuration by this proximal sleeve 14, which in turn is kept in a contracted configuration by the intermediate sheath 24.

By deploying inside the proximal sleeve 14, the distal sleeve 16 connects to this proximal sleeve 14.

It will be noted that in this position, the leaflets 13 of the native valve are inserted between the distal sleeve 16 and the proximal arms 18.

Figure 19:
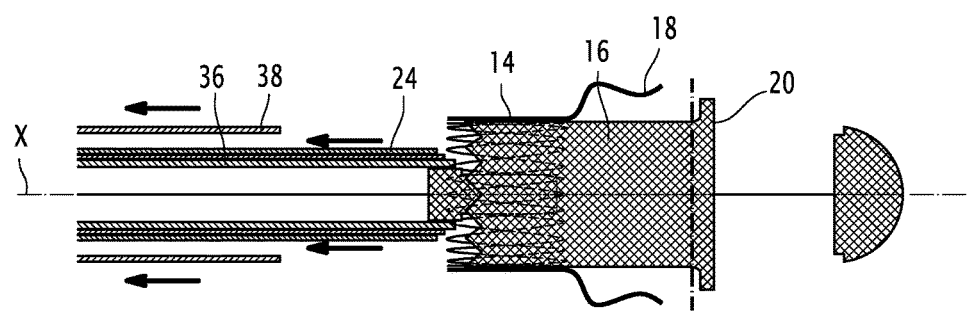

Once the proximal 14 and distal 16 sleeves are thus connected, the intermediate sheath 24 is retracted, so as to free the proximal sleeve 14, as shown in FIG. 19.

The proximal sleeve 14 then deploys radially to its deployed configuration, as well as the distal sleeve 16 inside this deployed proximal sleeve 14.

In this deployed configuration of the proximal sleeve 14, the maintaining means 22 release the proximal arms 18, which are then elastically returned toward their anchoring position, as previously described.

Figure 20:
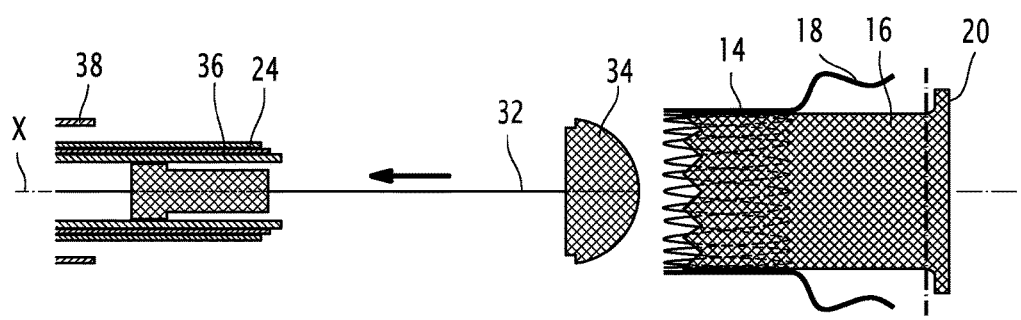

This being done, the axial fastening between the stay 32 and the proximal end of the implant 10 is freed. The stay 32, the head 34 and the rod are then removed from the patient through the inner conduit, as shown in FIG. 20.

It will be noted that, in this deployed configuration, the distal sleeve 16 extends longitudinally, partially inside the proximal sleeve 14, coaxially to that proximal sleeve 14, partially inside the receiving area 23, such that the tissue is received between the proximal arms 18 and the distal sleeve 16, and partially past the receiving area 23. This deployed configuration corresponds to that of FIG. 1.

Furthermore, the proximal sleeve 14 is arranged axially separated from the leaflets 13, inside the ventricular cavity.

It will be noted that the invention is not limited to the embodiments previously described.

In particular, it is possible to have other suitable forms for the first and second stops of maintaining means 22.

Furthermore, the invention can be applied to different forms of proximal arms 18.

For example, the invention could be applied to an implant whereof each proximal arm 18 comprises:
- a proximal part, starting axially from the connected end toward the proximal end of the proximal sleeve, bearing the first stop
- a bifurcation part, connecting the proximal segment to a distal part of the proximal arm
- the distal part, starting axially from the bifurcation part toward the distal end of the proximal sleeve.

Said distal part can also have a curved shape.

In that case, the proximal part and the bifurcation together define a deeper housing for the leaflets 13. Of course, the length of the proximal part can be chosen to be longer or shorter, depending on the desired depth of the housing.

According to another alternative, at least one proximal arm 18 has a distal region protruding radially away from the central axis X relative to an intermediate region of that proximal arm.

More particularly, at least one first proximal arm 18 has a first distal region applied across from a first distal arm 20, and a second proximal region 18 has a second distal region applied across from a second distal arm 20, the radial expanse of the first distal region being greater than the radial expanse of the second distal region.

Generally speaking, the radial expanse of the distal region of each proximal arm 18 can be chosen to be larger or smaller, in particular depending on the predetermined shape of the blood circulation passage designed to receive the implant.

According to another alternative, each proximal arm 18 includes an intermediate part that is elastically deformable in a longitudinal direction of the proximal arm 18. To that end, the intermediate part is generally in the form of a spring.

Owing to its longitudinally elastically deformable intermediate part, the length of each proximal arm 18 can vary, and adapt itself based on the position of the proximal sleeve 14 relative to the distal sleeve 16, in particular so as to ensure optimal pinching of the leaflets 13 between the proximal arms 18 and the distal arms 20. In other words, when there are no leaflets 13, it is possible to ensure contact between the free end 18B of at least one proximal arm 18 and a distal arm 20, in the deployed configuration and without outside bias.

According to another alternative, each proximal arm 16 includes an intermediate part bent so as to form an axial return defining a cavity. This cavity is designed to form a housing for the leaflets 13.

Any other form of proximal arms compatible with maintaining means 22 can be considered.

It will also be noted that the implant 10 can be installed according to an insertion method other than that previously described. In particular, the different installation steps of the proximal 14 and distal 16 sleeves can be carried out an order other than that previously described.

For example, the proximal arms 18 can be previously deployed, the outer sheath 38 being axially retracted to expose these proximal arms 18. In this case, the proximal sleeve 14 is kept in its contracted configuration, and the proximal arms 18, which are not subject to any outside bias, are then constrained in their separating position by the maintaining means 22, as previously described.

The separation of the proximal arms 18 is then done optimally so that the leaflets 13 are across from a receiving area 23 defined between these proximal arms 18. It should be noted that by starting in this way by installing the proximal arms 18, the manipulation is not bothered by the distal sleeve 16 and the elements allowing its installation.

The proximal sleeve 14, as well as the intermediate sheath 24 that surrounds it, are then moved toward the leaflets 13. These leaflets 13 are thus inserted into the receiving area 23 defined between the proximal arms 18.

Once the proximal arms 18 are suitably arranged, the head 34 and the downstream part of the tool 19 are then inserted into the atrial cavity, past the mitral annulus, such that the distal arms 20 are positioned in the atrial cavity past the mitral annulus. In this case, the distal arms 20 are kept in the contracted position by the inner sheath 36.

The inner sheath 36 is next axially retracted away from the head 34 relative to the intermediate sheath 24, and relative to the stay 32, to expose the distal arms 20, which are then deployed. The tool 19 is then moved toward the left ventricle to press the distal arms 20 against the atrial face of the leaflets 13.

Once the distal sleeve 16 is in place, the inner sheath 36 is retracted so as to free this distal sleeve. This distal sleeve 16 being positioned inside the proximal sleeve 14, it is kept in a contracted configuration by this proximal sleeve 14, which in turn is kept in a contracted configuration by the intermediate sheath 24.

By deploying inside the proximal sleeve 14, the distal sleeve 16 connects to this proximal sleeve 14.

It will be noted that in this position, the leaflets 13 of the native valve are inserted between the distal sleeve 16 and the proximal arms 18.

Once the proximal 14 and distal 16 sleeves are thus connected, the intermediate sheath 24 is retracted, so as to free the proximal sleeve 14. The proximal sleeve 14 then deploys radially to its deployed configuration, as well as the distal sleeve 16 inside this deployed proximal sleeve 14.

In this deployed configuration of the proximal sleeve 14, the maintaining means 22 release the proximal arms 18, which are then elastically returned toward their anchoring position, as previously described.

This being done, the axial fastening between the stay 32 and the proximal end of the implant 10 is freed. The stay 32, the head 34 and the rod are then removed from the patient through the inner conduit.

It is also possible to provide other release methods. For example, another release method is described in reference to FIGS. 21 to 26.

Figure 21:
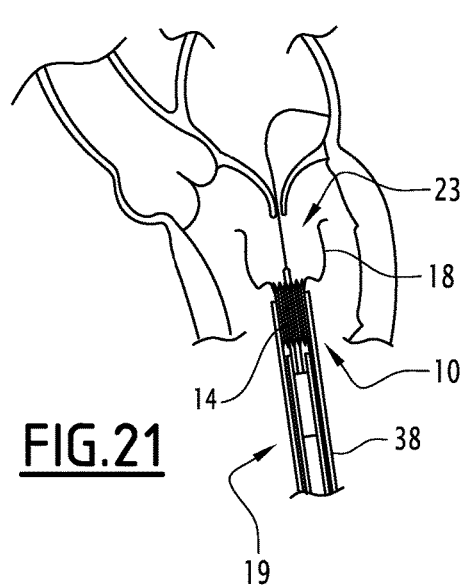

The release method includes inserting a distal end of the release tool 19, comprising the implant 10 in the contracted configuration, into the ventricular cavity. Next, as shown in FIG. 21, the outer sheath 38 is retracted axially so as to free the proximal arms 18, as previously described. The deployment of the proximal arms 18 defines a receiving area 23, which is then completely free.

It should be noted that the proximal arms 18 are deployed before the armature 12 is formed, i.e., before the proximal sleeve 14 is assembled with the distal sleeve 16.

Figure 22:
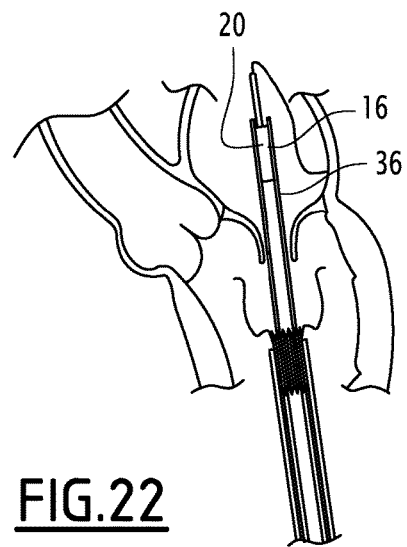

Next, as shown in FIG. 22, the inner sheath 36, containing the distal sleeve 16, is moved axially to the atrial cavity, through the mitral annulus, such that the distal arms 20 are positioned in the atrial cavity.

Figure 23:
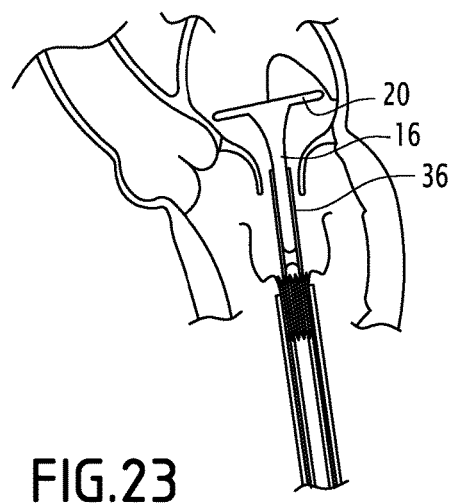

Then, as shown in FIG. 23, the inner sheath 36 is axially retracted so as to free the distal arms 20, which are then deployed. During this step, the atrial sleeve 16 remains partially contracted in the inner sheath 36.

Figure 24:
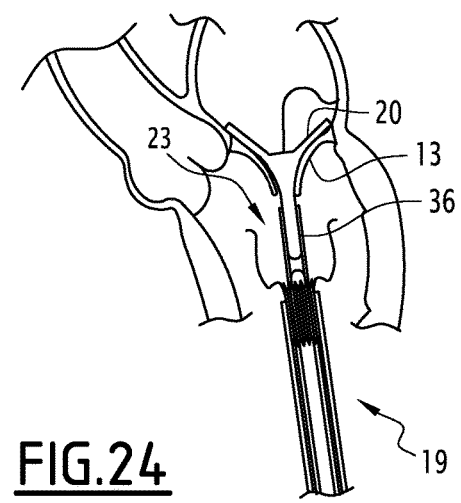

As shown in FIG. 24, the tool 19 is next moved toward the left ventricle to press the distal arms 20 against the atrial face of the leaflets 13. Thus, the distal arms 20 apply an axial force against the atrial face of the leaflets 13, this axial force being oriented from the atrial cavity toward the ventricular cavity.

Figure 25:
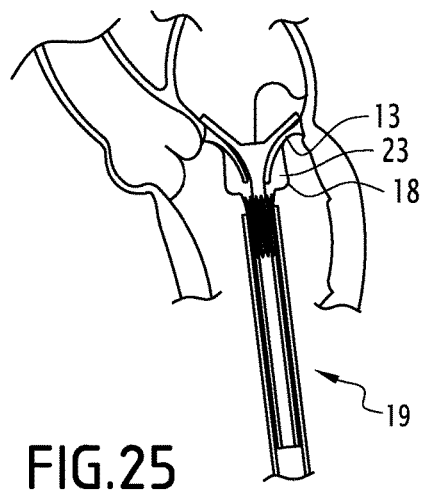

Then, the receiving area 23 is positioned across from the leaflets 13, such that these leaflets 13 are inserted into this receiving area 23 when the tool 19 is moved toward these leaflets 13, as shown in FIG. 25.

Thus, the proximal arms 18 are pressed against the ventricular face of the leaflets 13. Thus, the proximal arms 18 apply an axial force against the ventricular face of the leaflets 13, this axial force being oriented from the ventricular cavity toward the atrial cavity. The direction of the axial force applied by the proximal arms 18 is therefore opposite the direction of the axial force applied by the distal arms 20.

As previously indicated, the proximal sleeve 14 is axially movable relative to the distal sleeve 16, such that the relative position of the proximal sleeve 14 with respect to the distal sleeve 16 can be chosen based on the configuration of the blood circulation passage in which the implant is installed.

Figure 26:
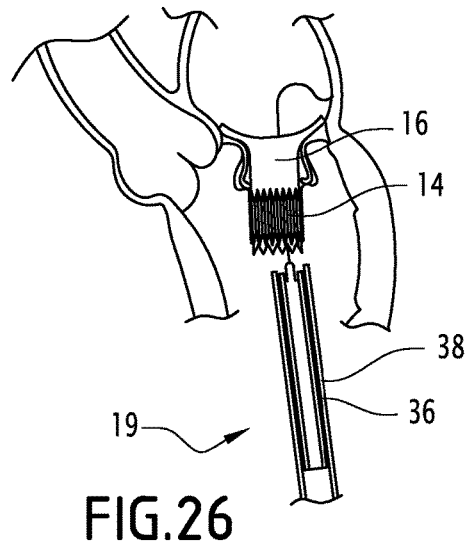

The position of the proximal sleeve 14 is adjusted, then the inner sheath 36 and the outer sheath 38 are retracted, such that the distal sleeve 16 and the proximal sleeve 14 are deployed, as shown in FIG. 26. It should be noted that the distal sleeve 16 and the proximal sleeve 14 can be deployed simultaneously, or alternatively the distal sleeve 16 is deployed inside the proximal sleeve 14 prior to the deployment of that proximal sleeve 14.

After the deployment of the proximal 14 and distal 16 sleeves, these proximal 14 and distal 16 sleeves are assembled, thus forming the armature 12. In other words, the armature 12 is only formed in the deployed configuration.

Once these deployments are done, the release tool is removed from the patient.

It is also possible to provide other installation methods for the implant.

In particular, the proximal sleeve 14 and the distal sleeve 16 forming two separate assemblies, it is possible to bring them into the blood circulation passage via two separate access routes.

For example, the distal sleeve 16 can be brought by the transvenous anterograde route, and thus inserted into the atrial cavity without passing through the ventricular cavity, and the proximal sleeve 14 can be brought by the transaortic retrograde route, and thus be inserted into the ventricular cavity without passing through the atrial cavity.

In this case, the treatment device includes a first release tool for the proximal sleeve 14 and a second release tool for the distal sleeve 16.

These first and second release tools have diameters smaller than the diameter of a release tool bearing both the proximal 14 and distal 16 sleeves. In other words, in this installation method, two access routes are provided that are narrower than the single access route necessary for the installation methods previously described.

Such an installation method via two separate access routes is described in reference to FIGS. 27 to 32.

First, a first part 19A of the release tool, comprising an outer sheath 38 and the proximal sleeve 14 in the contracted configuration inside this outer sheath 38, are inserted into the ventricular cavity by a first route.

Figure 27:
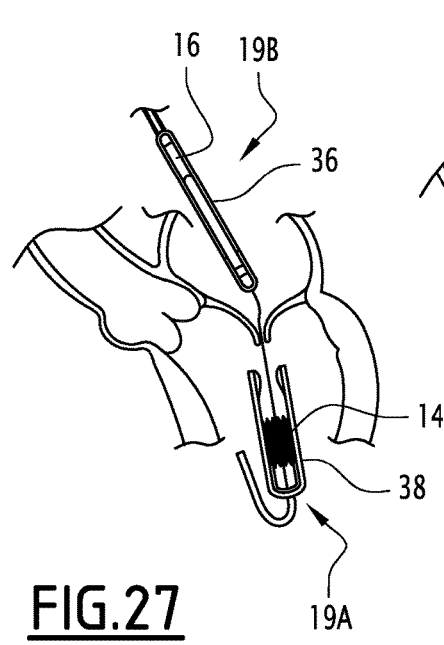

Next, as shown in FIG. 27, a second part 19B of the release tool, comprising an inner sheath 36 and the distal sleeve 16 in the contracted configuration inside the inner sheath 36, are inserted into the atrial cavity by a second route different from the first route.

Thus, according to this installation method, the second part 19B of the release tool is not inserted through the mitral annulus into the atrial cavity.

The outer sheath 38 is next axially retracted so as to release the proximal arms 18, which are thus deployed as previously described. The deployment of the proximal arms 18 thus defines the receiving area 23.

Figure 28:
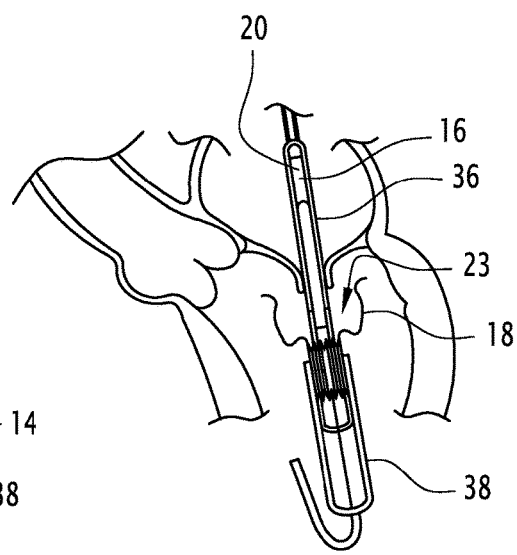

Next, as shown in FIG. 28, the inner sheath 36 containing the distal sleeve 16 is moved axially to the ventricular cavity, past the mitral annulus, such that the distal arms 20 remain positioned in the atrial cavity, and the distal sleeve 16 is partly positioned in the ventricular cavity.

Figures 29, 30:
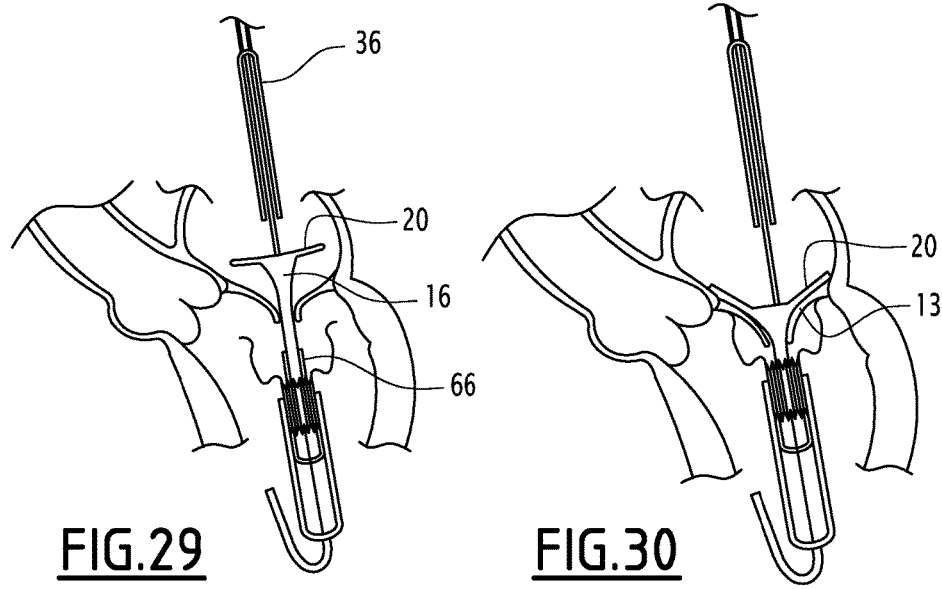

Next, as shown in FIG. 29, the inner sheath 36 is retracted axially so as to free the distal arms 20, which are then deployed. During this step, the distal sleeve 16 remains partially contracted, for example owing to an annular maintaining element 66 surrounding this distal sleeve 16.

The distal arms 20 are next pressed against the atrial face of the leaflets 13, as shown in FIG. 30. Thus, the distal arms 20 apply an axial force against the atrial face of the leaflets 13, this axial force being oriented from the atrial cavity toward the ventricular cavity.

Figures 31, 32:
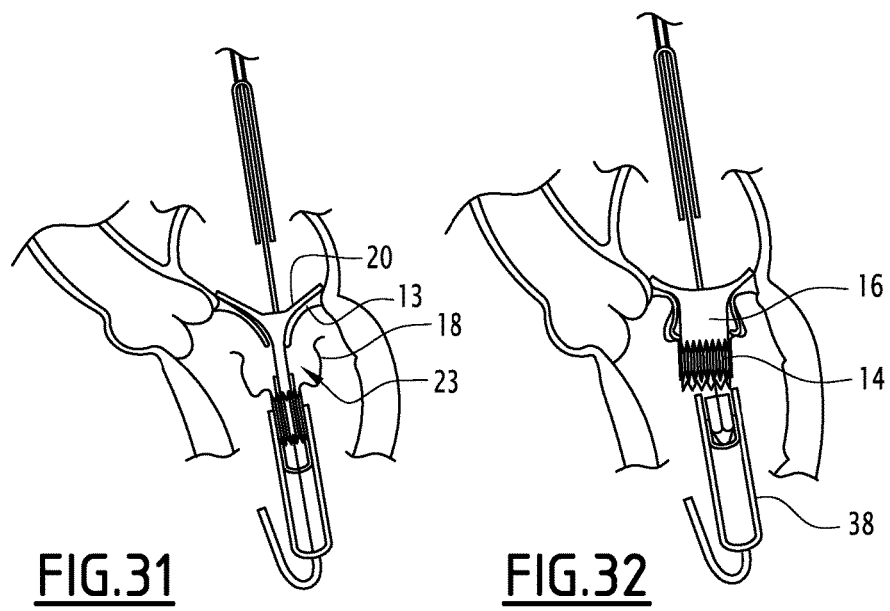

The receiving area 23 is next positioned across from the leaflets 13, such that the latter are inserted into this receiving area 23 when the first part 14A of the release tool is moved toward these leaflets 13, as shown in FIG. 31. Then, the receiving area 23 is positioned across from the leaflets 13, such that these leaflets 13 are inserted into this receiving area 23 when the tool 19 is moved toward these leaflets 13, as shown in FIG. 25.

Thus, the proximal arms 18 are pressed against the ventricular face of the leaflets 13. Thus, the proximal arms 18 apply an axial force against the ventricular face of the leaflets 13, this axial force being oriented from the ventricular cavity toward the atrial cavity. The direction of the axial force applied by the proximal arms 18 is therefore opposite the direction of the axial force applied by the distal arms 20.

As previously indicated, the proximal sleeve 14 is axially movable relative to the distal sleeve 16, such that the relative position of the proximal sleeve 14 with respect to the distal sleeve 16 can be chosen based on the configuration of the blood circulation passage in which the implant is installed.

The position of the proximal sleeve 14 is adjusted, then the annular maintaining element 66 and the outer sheath 38 are retracted, such that the distal sleeve 16 and the proximal sleeve 14 are deployed, as shown in FIG. 32.

It should be noted that the distal sleeve 16 and the proximal sleeve 14 can be deployed simultaneously, or alternatively the distal sleeve 16 is deployed inside the proximal sleeve 14 prior to the deployment of that proximal sleeve 14.

After the deployment of the proximal 14 and distal 16 sleeves, these proximal 14 and distal 16 sleeves are assembled, thus forming the armature 12. In other words, the armature 12 is only formed in the deployed configuration.

Once these deployments are done, the release tool is removed from the patient, each of its parts through the corresponding route.

The invention claimed is:

1. An implant designed to be placed in a blood circulation passage, and to be fastened on a tissue, and comprising:
   a proximal sleeve, generally tubular around a central axis, extending longitudinally between a proximal end and a distal end, the proximal sleeve being deployable between a contracted configuration and a deployed configuration,
   a plurality of proximal arms, each extending between a connected end connected to the distal end of the proximal sleeve (14), and a free end designed to bear on a first face of the tissue, each proximal arm extending in the direction of the central axis such that its free end is positioned beyond the distal end of the proximal sleeve,
   a distal sleeve, with a generally tubular shape around the central axis, deployable between a contracted configuration and a deployed configuration, designed to be assembled with the proximal sleeve to form a tubular armature together, that armature defining an internal blood circulation conduit when the proximal sleeve and the distal sleeve are assembled and each in the deployed configuration,
   a plurality of distal arms, supported by the distal sleeve, and extending substantially perpendicular to the central axis in the deployed configuration, designed to bear on a second face of the tissue, such that the tissue is then pinched between the proximal arms and the distal arms, wherein:
   at least one of the proximal arms is a deformable proximal arm, elastically deformable between a separating position and an anchoring position, such that, when there is no outside bias, the radial distance between its free end and its connected end is larger in the separated position rather than in the anchoring position, this deformable proximal arm being elastically returned toward its anchoring position,
   the implant includes a first stop and a second stop for maintaining said at least one deformable proximal arm in its separating position, wherein:
      the first stop is supported by said deformable proximal arm, and
      the second stop is designed to cooperate with the first stop when the proximal sleeve is in the contracted configuration to keep that deformable proximal arm in its separating position, and to release that first stop when the proximal sleeve is in the deployed configuration to allow the deformable proximal arm to move toward its anchoring position,
   and wherein the first stop of the deformable proximal arm extends laterally relative to that deformable proximal arm, the first stop preferably being arranged near the connected end of that deformable proximal arm.

2. The implant according to claim 1, wherein the second stop is supported by the proximal sleeve.

3. The implant according to claim 2, wherein the proximal sleeve is formed by different filiform elements arranged in a grid, forming cells (M), each deformable proximal arm provided with a first stop being arranged circumferentially on the proximal sleeve between two consecutive cells, the corresponding second stop being supported by at least one of the filiform elements forming those two consecutive cells, these filiform elements being brought closer to one another in the contracted configuration, such that the second stop cooperates with the first stop, and separated from one another in the deployed configuration, so as to leave a radial passage for the first stop, thus releasing that first stop.

4. The implant according to claim 1, wherein the proximal sleeve supports at least two deformable proximal arms each provided with a first stop, such that the distance between the first stop and the connected end of one of those two deformable proximal arms (18) is greater than the distance between the first stop and the connected end of the other of those two deformable proximal arms.

5. The implant according to claim 1, wherein the first stop of at least one of the deformable proximal arms is formed by a protruding part of that deformable proximal arm, extending laterally relative to that deformable proximal arm.

6. The implant according to claim 1, wherein the first stop of at least one of the deformable proximal arms is formed by an element attached on that deformable proximal arm, that element extending laterally relative to that deformable proximal arm.

7. A treatment device for a blood circulation passage, including an implant and a tool for releasing the implant, wherein the implant is designed to be placed in a blood circulation passage, and to be fastened on a tissue, and comprises:
   a proximal sleeve, generally tubular around a central axis, extending longitudinally between a proximal end and a distal end, the proximal sleeve being deployable between a contracted configuration and a deployed configuration,
   a plurality of proximal arms, each extending between a connected end connected to the distal end of the proximal sleeve, and a free end designed to bear on a first face of the tissue, each proximal arm extending in the direction of the central axis such that its free end is positioned beyond the distal end of the proximal sleeve,
   a distal sleeve, with a generally tubular shape around the central axis, deployable between a contracted configuration and a deployed configuration, designed to be assembled with the proximal sleeve to form a tubular armature together, that tubular armature defining an internal blood circulation conduit when the proximal sleeve and the distal sleeve are assembled and each in the deployed configuration,
   a plurality of distal arms, supported by the distal sleeve, and extending perpendicular to the central axis in the deployed configuration, designed to bear on a second face of the tissue, such that the tissue is then pinched between the proximal arms and the distal arms, wherein:
   at least one of the proximal arms is a deformable proximal arm, elastically deformable between a separating position and an anchoring position, such that, when there is no outside bias, the radial distance between its free end and its connected end is larger in the separated position rather than in the anchoring position, this proximal arm being elastically returned toward its anchoring position, the implant includes a first stop and a second stop for
maintaining said at least one deformable proximal arm
in its separating position, wherein:
- the first stop is supported by said deformable proximal arm, and
- the second stop is designed to cooperate with the first stop when the proximal sleeve is in the contracted configuration to keep that at least one deformable proximal arm in its separating position, and to release that first stop when the proximal sleeve is in the deployed configuration to allow the at least one deformable proximal arm to move toward its anchoring position, wherein the proximal and distal sleeves are mounted in their respective contracted configurations in the release tool, and wherein:
- the release tool includes a sheath for maintaining each deformable proximal arm provided with a first stop in its separating position,
- said maintaining sheath has a general shape of revolution around the longitudinal axis, and is designed to be positioned around the proximal sleeve in the contracted configuration,
- said maintaining sheath includes longitudinal strips separated by longitudinal openings, each longitudinal strip being designed to pass through an opening provided in a respective proximal arm,
- each longitudinal strip includes a second stop designed to cooperate with the first stop of the proximal arm through which that longitudinal strip passes.

8. The treatment device according to claim 7, wherein said longitudinal strip is provided with a boss, protruding radially toward the outside of the maintaining sheath, bearing said second stop.

9. A method for installing an implant on the leaflets of a native valve, between an atrial cavity and a ventricular cavity of the heart, the leaflets having an atrial face and a ventricular face, the implant comprising:
- a proximal sleeve, generally tubular around a central axis, extending longitudinally between a proximal end and a distal end, the proximal sleeve being deployable between a contracted configuration and a deployed configuration,
- a plurality of proximal arms, each extending between a connected end connected to the distal end of the proximal sleeve, and a free end designed to bear on a first face of the tissue, each proximal arm extending in the direction of the central axis such that its free end is positioned beyond the distal end of the proximal sleeve,
- a distal sleeve, with a generally tubular shape around the central axis, deployable between a contracted configuration and a deployed configuration, designed to be assembled with the proximal sleeve to form a tubular armature together, that tubular armature defining an internal blood circulation conduit when the proximal sleeve and the distal sleeve are assembled and each in the deployed configuration,
- a plurality of distal arms, supported by the distal sleeve, and extending perpendicular to the central axis in the deployed configuration, designed to bear on a second face of the tissue, such that the tissue is then pinched between the proximal arms and the distal arms, wherein:
- at least one of the proximal arms is a deformable proximal arm, elastically deformable between a separating position and an anchoring position, such that, when there is no outside bias, the radial distance between its free end and its connected end is larger in the separated position rather than in the anchoring position, this proximal arm being elastically returned toward its anchoring position, the implant includes a first stop and a second stop for maintaining said at least one deformable proximal arm in its separating position, wherein:
- the first stop is supported by said deformable proximal arm, and
- the second stop is designed to cooperate with the first stop when the proximal sleeve is in the contracted configuration to keep that at least one deformable proximal arm in its separating position, and to release that first stop when the proximal sleeve is in the deployed configuration to allow the at least one deformable proximal arm to move toward its anchoring position, and the method including:
- positioning the distal arms in the atrial cavity,
- deploying said distal arms in the atrial cavity,
- pressing the distal arms against the atrial face of the leaflets,
- moving the proximal sleeve toward the leaflets, with the proximal arms deployed so as to define a receiving space for the leaflets, in order to insert the leaflets into the receiving space, and pressing the proximal arms against the ventricular face of the leaflets by applying an axial force toward those leaflets,
- deploying the distal sleeve and the proximal sleeve, and assembling the distal sleeve with the proximal sleeve so as to form a tubular armature of the implant.

10. The method of claim 9, using a release tool in which the implant is housed in the contracted position, the tool including:
- an inner sheath for keeping the distal sleeve in the contracted configuration, and keeping the distal arms in the axial configuration,
- an outer sheath for keeping the proximal sleeve in the contracted configuration, the method including:
- deploying the proximal arms, in particular by retracting the outer sheath so as to release the proximal arms,
- positioning the distal arms in the atrial cavity, while the inner sheath is still positioned around the distal arms,
- deploying the distal arms in the atrial cavity, while retracting the inner sheath so as to free those distal arms,
- pressing the distal arms against the atrial face of the leaflets, by moving the tool toward the ventricular cavity so as to apply an axial force toward that ventricular cavity,
- moving the proximal sleeve toward the leaflets, while the outer sheath covers the proximal sleeve, and pressing the proximal arms against the ventricular face of the leaflets to apply an axial force oriented toward the atrial cavity, and
- applying the proximal and distal sleeves, while retracting the inner and outer sheaths.

11. The method of claim 10, wherein:
- positioning the distal arms in the atrial cavity takes place after deploying the proximal arms,
- deploying the distal arms in the atrial cavity takes place after positioning the distal arms in the atrial cavity,
- pressing the distal arms against the atrial face of the leaflets follows deploying the distal arms in the atrial cavity,
- moving the proximal sleeve toward the leaflets is done following the pressing of the distal arms against the atrial face of the leaflets, deploying the proximal and distal sleeves takes place after moving the proximal sleeve toward the leaflets.

12. The method of claim 10, wherein:

the outer sheath and the proximal sleeve in the contracted configuration in the outer sheath are introduced into the ventricular cavity by a first route, and the inner sheath and the distal sleeve in the contracted configuration in the inner sheath are introduced into the atrial cavity by a second route different from the first.

13. The method of claim 9, wherein the native valve is chosen between a mitral valve or a tricuspid valve.

* * * * *